(12) United States Patent
Keerthivasan et al.

(10) Patent No.: US 11,454,687 B2
(45) Date of Patent: Sep. 27, 2022

(54) MULTI-ECHO RADIAL LOOK-LOCKER IMAGING FOR SIMULTANEOUS T1 AND FAT FRACTION QUANTIFICATION

(71) Applicant: Siemens Healthcare GmbH, Erlangen (DE)

(72) Inventors: Mahesh Bharath Keerthivasan, Tucson, AZ (US); Xiaodong Zhong, Oak Park, CA (US); Marcel Dominik Nickel, Herzogenaurach (DE); Vibhas S. Deshpande, Austin, TX (US)

(73) Assignee: Siemens Healthcare GmbH, Erlangen (DE)

( * ) Notice: Subject to any disclaimer, the term of this patent is extended or adjusted under 35 U.S.C. 154(b) by 178 days.

(21) Appl. No.: 16/837,216

(22) Filed: Apr. 1, 2020

(65) Prior Publication Data
US 2021/0311145 A1    Oct. 7, 2021

(51) Int. Cl.
*G01R 33/48* (2006.01)
*G06T 11/00* (2006.01)
(Continued)

(52) U.S. Cl.
CPC .......... *G01R 33/4828* (2013.01); *A61B 5/055* (2013.01); *G01R 33/4824* (2013.01);
(Continued)

(58) Field of Classification Search
CPC ................. G01R 33/4828; G01R 33/4824; G01R 33/50; G01R 33/5607; A61B 5/05;
(Continued)

(56) References Cited

U.S. PATENT DOCUMENTS 9,823,322 B2    11/2017    Kannengiesser et al.
2015/0042334 A1    2/2015    Kannengiesser et al.
(Continued)

OTHER PUBLICATIONS

Marty, Benjamin, and Pierre G. Carlier. "MR fingerprinting for water T1 and fat fraction quantification in fat infiltrated skeletal muscles." Magnetic resonance in medicine 83.2 (Sep. 10, 2019): 621-634. (Year: 2019).*

(Continued)

*Primary Examiner* — Rishi R Patel (57) ABSTRACT

A method for using a multi-echo magnetic resonance imaging (MRI) simultaneously quantify T1 and fat fraction in an anatomical region of interest includes performing a radial single shot multi-echo acquisition of the anatomical region of interest. The radial single shot multi-echo acquisition comprises applying a preparation pulse to invert longitudinal magnetization of the anatomical region of interest, and acquiring a plurality of radial readouts at different echo times (TE). A magnetization recovery curve is continuously sampled using the plurality of radial readouts to yield a plurality of radial spokes. The radial spokes for each TE are ground together to generate under-sampled k-space data for each TE. The under-sampled k-space data is reconstructed into a plurality of multi-echo images corresponding to the different echo times. One or more fitting algorithms are applied to the multi-echo images to generate a water-only T1 map and a proton density fat fraction (PDFF) measurement.

18 Claims, 10 Drawing Sheets

(51) Int. Cl.
  *A61B 5/055* (2006.01)
  *G01R 33/50* (2006.01)
  *G01R 33/56* (2006.01)

(52) U.S. Cl.
  CPC ......... *G01R 33/50* (2013.01); *G01R 33/5607* (2013.01); *G06T 11/005* (2013.01); *G06T 11/006* (2013.01); *G06T 2210/41* (2013.01); *G06T 2211/424* (2013.01)

(58) Field of Classification Search
  CPC . G06T 11/005; G06T 11/006; G06T 2210/41; G06T 2211/424
  See application file for complete search history.

(56) References Cited

U.S. PATENT DOCUMENTS

| | | | |
|---|---|---|---|
| 2018/0204045 A1* | 7/2018 | Feiweier | G01R 33/5608 |
| 2018/0275235 A1 | 9/2018 | Reeder et al. | |
| 2021/0181286 A1* | 6/2021 | Nickel | G16H 30/20 |

OTHER PUBLICATIONS

Wang, Xiaoqing, et al. "High-resolution myocardial T 1 mapping using single-shot inversion recovery fast low-angle shot MRI with radial undersampling and iterative reconstruction." The British journal of radiology 89.1068 (2016): 20160255. (Year: 2016).*
Ding, Y., et al. "Liver fibrosis staging using T1 mapping on gadoxetic acid-enhanced MRI compared with DW imaging." Clinical radiology 70.10 (2015): 1096-1103.
Katsube, Takashi, et al. "Estimation of liver function using T1 mapping on Gd-EOB-DTPA-enhanced magnetic resonance imaging." Investigative radiology 46.4 (2011): 277-283.
Li, Zhao, et al. "Rapid high-resolution T1 mapping using a highly accelerated radial steady-state free-precession technique." Journal of Magnetic Resonance Imaging 49.1 (2019): 239-252.
Thompson,Richard B. Simultaneous Proton Density Fat Fraction Imaging and Water T1-Mapping with Low B1+ Sensitivity (PDFF-T1). Proceedings of the ISMRM #0035, 2018.
Mozes, Ferenc E., et al. "Mapping tissue water T1 in the liver using the MOLLI T1 method in the presence of fat, iron and B0 inhomogeneity." NMR in Biomedicine 32.2 (2019): e4030.
Kamimura, Kiyohisa, et al. "Quantitative evaluation of liver function with T1 relaxation time index on Gd-EOB-DTPA-enhanced MRI: Comparison with signal intensity-based indices." Journal of Magnetic Resonance Imaging 40.4 (2014): 884-889.
Cassinotto, Christophe, et al. "MR relaxometry in chronic liver diseases: comparison of T1 mapping, T2 mapping, and diffusion-weighted imaging for assessing cirrhosis diagnosis and severity." European journal of radiology 84.8 (2015): 1459-1465.
Banerjee R, Pavlides M, Tunnicliffe EM, et al. "Multiparametric magnetic resonance for the non-invasive diagnosis of liver disease." J Hepatol. 2014;60(1):69-77.
Deoni, Sean CL, Brian K. Rutt, and Terry M. Peters. "Rapid combined T1 and T2 mapping using gradient recalled acquisition in the steady state." Magnetic Resonance in Medicine: An Official Journal of the International Society for Magnetic Resonance in Medicine 49.3 (2003): 515-526.

Cheng, Hai-Ling Margaret, and Graham A. Wright. "Rapid high-resolution T1 mapping by variable flip angles: accurate and precise measurements in the presence of radiofrequency field inhomogeneity." Magnetic Resonance in Medicine: An Official Journal of the International Society for Magnetic Resonance in Medicine 55.3 (2006): 566-574.
Liberman, Gilad, Yoram Louzoun, and Dafna Ben Bashat. "T1 mapping using variable flip angle SPGR data with flip angle correction." Journal of Magnetic Resonance Imaging 40.1 (2014): 171-180.
Messroghli, Daniel R., et al. "Modified Look-Locker inversion recovery (MOLLI) for high-resolution T1 mapping of the heart." Magnetic Resonance in Medicine: An Official Journal of the International Society for Magnetic Resonance in Medicine 52.1 (2004): 141-146.
Deichmann, R., and A. Haase "Quantification of T1 values by Snapshot-Flash NMR imaging." Journal of Magnetic Resonance (1969) 96.3 (1992): 608-612.
Lugauer, Felix, et al. "Single-breath-hold abdominal T1 mapping using 3D Cartesian Look-Locker with spatiotemporal sparsity constraints." Magnetic Resonance Materials in Physics, Biology and Medicine 31.3 (2018): 399-414.
Wang, Xiaoqing, et al. "Single-shot multi-slice T1 mapping at high spatial resolution-inversion-recovery FLASH with radial undersampling and iterative reconstruction." The Open Medical Imaging Journal 9.1 (2015).
Karampinos, Dimitrios C., et al. "T1-corrected fat quantification using chemical shift-based water/fat separation: application to skeletal muscle." Magnetic resonance in medicine 66.5 (2011): 1312-1326.
Leporq, Benjamin, et al. "Liver fat volume fraction quantification with fat and water T 1 and T 2* estimation and accounting for NMR multiple components in patients with chronic liver disease at 1.5 and 3.0 T." European radiology 23.8 (2013): 2175-2186.
Altbach, Maria I., et al. "Processing of radial fast spin-echo data for obtaining T2 estimates from a single k-space data set." Magnetic Resonance in Medicine: An Official Journal of the International Society for Magnetic Resonance in Medicine 54.3 (2005): 549-559.
Grimm, Robert et. al.: "Self-gated MRI motion modeling for respiratory motion compensation in integrated PET/MRI"; Medical Image Analysis; vol. 19, pp. 110-120; 2015.
Shao, Jiaxin, et al. "Myocardial T1 mapping at 3.0 tesla using an inversion recovery spoiled gradient echo readout and bloch equation simulation with slice profile correction (BLESSPC) T1 estimation algorithm." Journal of Magnetic Resonance Imaging 43.2 (2016): 414-425.
Hu, Houchun H., et al. "Comparison of fat-water MRI and single-voxel MRS in the assessment of hepatic and pancreatic fat fractions in humans." Obesity 18.4 (2010): 841-847.
Yu, Huanzhou, et al. "Combination of complex-based and magnitude-based multiecho water-fat separation for accurate quantification of fat-fraction." Magnetic resonance in medicine 66.1 (2011): 199-206.
Hernando, Diego, et al. "Robust water/fat separation in the presence of large field inhomogeneities using a graph cut algorithm." Magnetic Resonance in Medicine: An Official Journal of the International Society for Magnetic Resonance in Medicine 63.1 (2010): 79-90.

* cited by examiner

MULTI-ECHO RADIAL LOOK-LOCKER IMAGING FOR SIMULTANEOUS T1 AND FAT FRACTION QUANTIFICATION

TECHNOLOGY FIELD

The present invention relates generally to methods, systems, and apparatuses for implementing multi-echo radial look-locker imaging for simultaneous T1 and fat fraction quantification in magnetic resonance imaging (MRI) systems. The techniques described herein may be used, for example, to estimate T1 maps using magnetization preparation schemes such as inversion or saturation recovery preparation.

BACKGROUND

Quantitative T1 estimation is becoming popular for abdominal imaging applications for the characterization of fatty liver disease, abdominal neoplasms, and liver fibrosis. Various techniques have been proposed for T1 estimation in body imaging. One of the more commonly used techniques is the multi-flip angle approach which acquires gradient echo images at two or more excitation flip angles and fits them to estimate the T1. While this method has been applied in breath-held T1 mapping, the estimated value is affected by B1 inhomogeneity variations. Alternately, B1 correction schemes have also been proposed to improve estimation accuracy. Look-Locker sampling-based techniques have also been adapted for abdominal imaging. These approaches typically use an inversion recovery preparation pulse to invert the longitudinal magnetization, followed by data acquisition at various inversion times. Inversion recovery-based schemes such as Modified Look-Locker inversion recovery (MOLLI) use a segmented acquisition scheme for data acquisition. Alternately, techniques such as SNAP-SHOT-Fast Low Angle Shot (FLASH), 3D Look-Locker, and radial Look-Locker imaging use a continuous data acquisition scheme following the inversion pulse. The use of Cartesian sampling schemes has restricted use of the above techniques to breath-held abdominal imaging.

Figure 1:
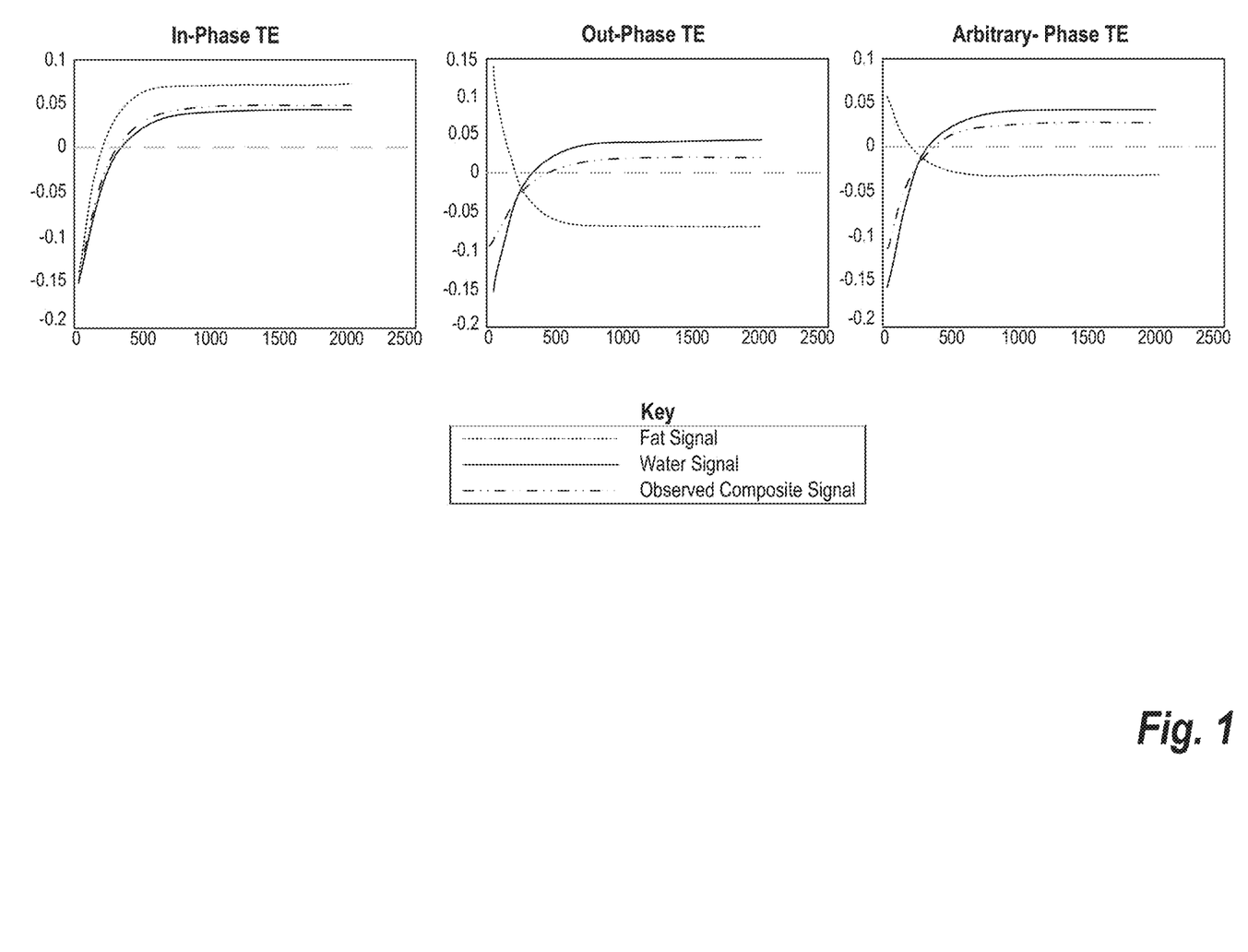
FIG. 1 illustrates the effect of echo time on observed inversion recovery signal from fat and water components.

The estimated T1 relaxation times are affected by presence of fat and iron in the liver. Based on the echo time used for data acquisition, T1 values are either under-estimated or over-estimated (see FIG. 1) necessitating the need for techniques to estimate water-only T1 values. The use of proton density fat fraction (PDFF) estimates from a separate spectroscopy acquisition to compute water-only T1 (T1w) values from a shortened-MOLLI technique have been proposed. Multi-echo acquisition strategies such as multi-echo saturation recovery and multi-echo variable flip angle gradient echo have been proposed for simultaneous quantification of fat-fraction and T1w values. The magnetization preparation-based techniques use steady-state free precession (SSFP) readouts which are more sensitive to off-resonance effects and the choice of echo times (TE). While the above methods have been proposed for breath-held abdominal imaging, they have a reduced slice efficiency and the use of Cartesian sampling schemes makes them more sensitive to motion artifacts.

SUMMARY

Embodiments of the present invention address and overcome one or more of the above shortcomings and drawbacks, by providing methods, systems, and apparatuses related to multi-echo radial Look-Locker imaging for simultaneous T1 and fat fraction quantification.

According to some embodiments, a method for using a multi-echo magnetic resonance imaging (MRI) simultaneously quantify T1 and fat fraction in an anatomical region of interest includes performing a radial single shot multi-echo acquisition of the anatomical region of interest. The radial single shot multi-echo acquisition comprises applying a preparation pulse to invert longitudinal magnetization of the anatomical region of interest, and acquiring a plurality of radial readouts at different echo times (TE). A magnetization recovery curve is continuously sampled using the plurality of radial readouts to yield a plurality of radial spokes. The radial spokes for each TE are ground together to generate under-sampled k-space data for each TE. The under-sampled k-space data is reconstructed into a plurality of multi-echo images corresponding to the different echo times. One or more fitting algorithms are applied to the multi-echo images to generate a water-only T1 map and a proton density fat fraction (PDFF) measurement.

According to other embodiments, a multi-echo MRI system for simultaneously quantifying T1 and fat fraction in an anatomical region of interest comprises an imaging device and one or more computers. The imaging device is configured to perform a radial single shot multi-echo acquisition of the anatomical region of interest. This radial single shot multi-echo acquisition comprises applying a preparation pulse to invert longitudinal magnetization of the anatomical region of interest, acquiring a plurality of radial readouts at different TEs, and continuously sampling a magnetization recovery curve using the plurality of radial readouts to yield a plurality of radial spokes. The computers are configured to group the radial spokes for each TE together to generate under-sampled k-space data for each TE, and reconstruct the under-sampled k-space data into a plurality of multi-echo images corresponding to the different echo times. The computers apply one or more fitting algorithms to the multi-echo images to generate a water-only T1 map and a PDFF measurement.

Additional features and advantages of the invention will be made apparent from the following detailed description of illustrative embodiments that proceeds with reference to the accompanying drawings.

BRIEF DESCRIPTION OF THE DRAWINGS

The foregoing and other aspects of the present invention are best understood from the following detailed description when read in connection with the accompanying drawings. For the purpose of illustrating the invention, there is shown in the drawings embodiments that are presently preferred, it being understood, however, that the invention is not limited to the specific instrumentalities disclosed. Included in the drawings are the following Figures.

DETAILED DESCRIPTION OF ILLUSTRATIVE EMBODIMENTS

The following disclosure describes the present invention according to several embodiments directed at methods, systems, and apparatuses for implementing multi-echo radial Look-Locker imaging for simultaneous T1 and fat fraction quantification. The technique described herein allows for the estimation of T1 maps using magnetization preparation schemes such as inversion or saturation recovery preparation. As described in further detail below, several different fitting approaches may be employed for estimating PDFF, T2* and a T1 water (T1w) map from data acquired at multiple TE times along the magnetization recovery curve. For 2-echo acquisitions, T2* can be assumed as known (typically set to infinity, i.e., neglecting T2* relaxation).

Figure 2A:
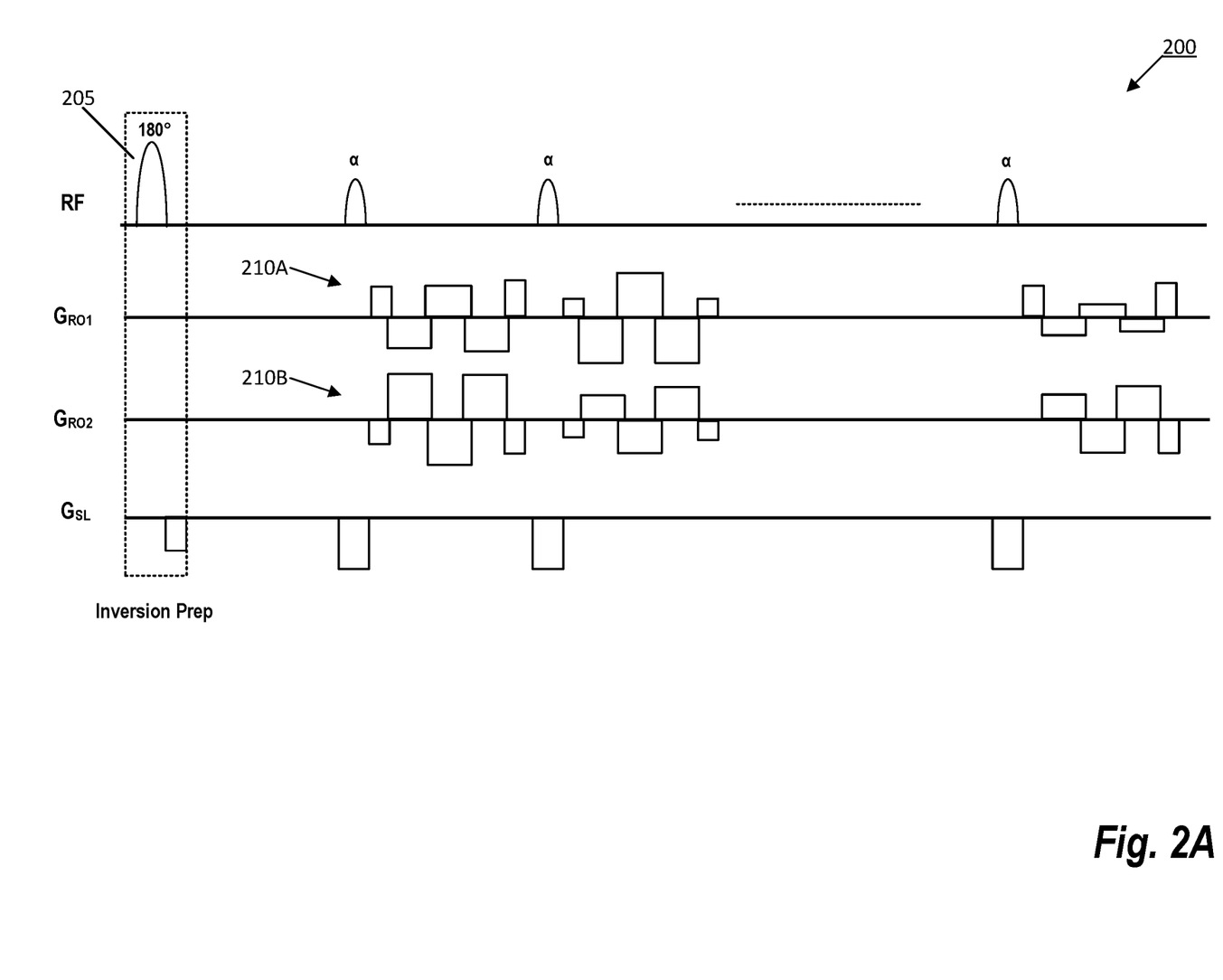
FIG. 2A shows an pulse sequence diagram for an inversion-recovery multi-echo radial Look-Locker T1 Mapping technique, according to some embodiments.

FIG. 2A shows an example pulse sequence and data sampling scheme for a 3-echo inversion recovery radial Look-Locker technique. In the radial single shot multi-echo acquisition 200 shown in FIG. 2A, RF denotes RF signals to be transmitted to an object; $G_{SL}$ denotes slice gradient magnetic field pulses to be applied to the object for slice selection; and $G_{RO1}$ and $G_{RO2}$ demote readout gradient magnetic field pulses to be applied the object for readout of echo data.

Following inversion preparation with a preparation pulse 205, the magnetization curve is sampled continuously using radial readouts 210 at different echo times (TE). The acquired radial spokes for each TE are grouped together to generate under-sampled k-space data which may then be reconstructed, for example, using either a tiered view sharing approach or iterative reconstruction algorithms. Thus, data acquired with the multi-echo radial Look-Locker imaging technique described herein generates co-registered images at different TEs and inversion times. It should be noted that, while the multi-echo radial Look-Locker imaging technique is described with reference to an inversion pulse, a saturation pulse may also be used for simultaneous quantification of T1, PDFF, and T2* in some embodiments of the present invention.

Figure 2B:
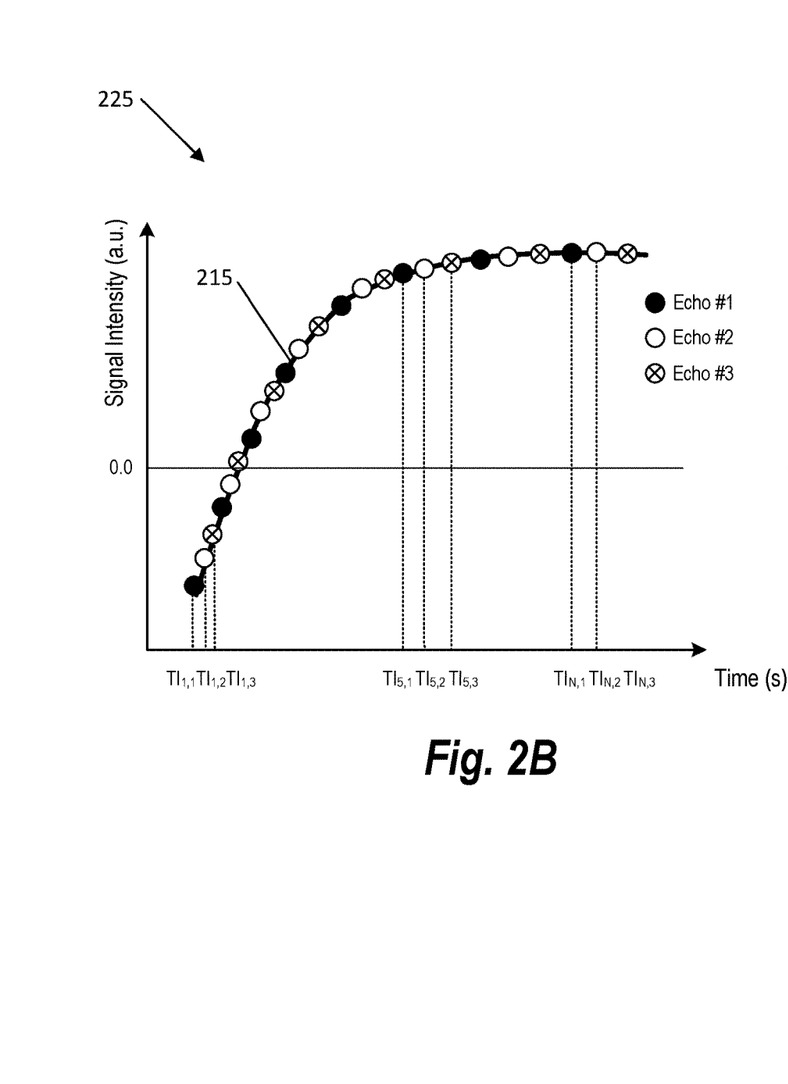
FIG. 2B shows a uniform sampling of the inversion recovery curve, according to some embodiments.
Figure 2C:
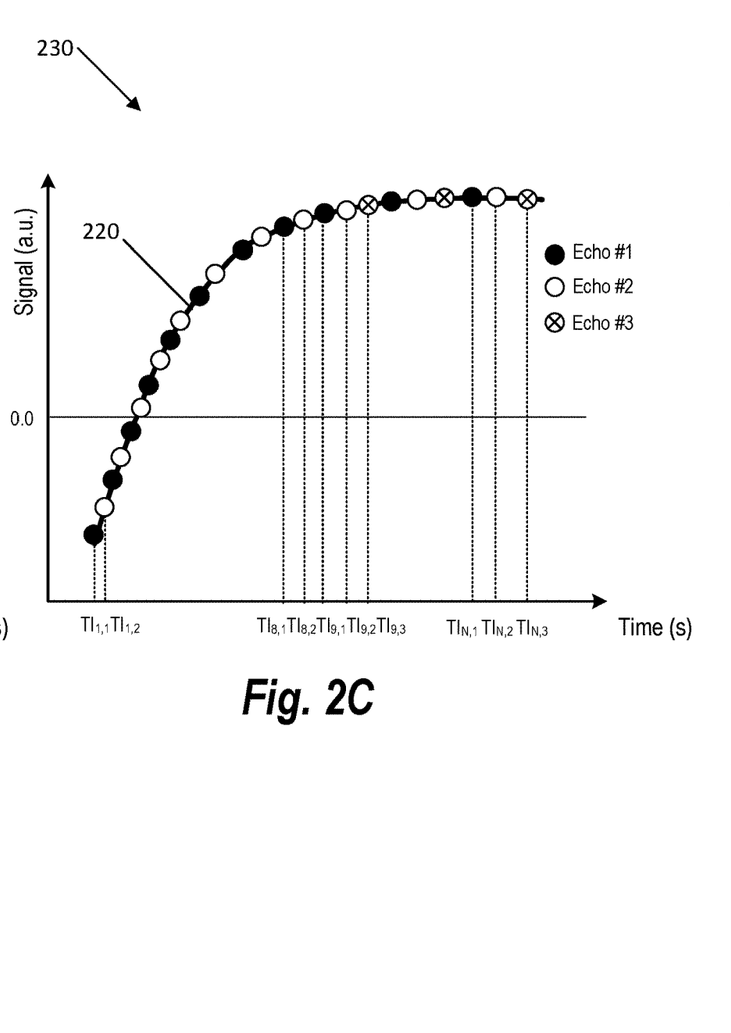
FIG. 2C shows an adaptive non-uniform sampling of the inversion recovery curve, according to some embodiments.

FIGS. 2B and 2C show two alternative schemes 225, 230 of sampling of the magnetization recovery curve. In the sampling scheme 225 shown in FIG. 2B, a uniform multi-echo acquisition is performed and the magnetization recovery curve 215 is uniformly sampled using the same number of echoes. However, the efficiency of this technique can be improved by using an adaptive non-uniform multi-echo sampling scheme where the initial part of the recovery curve 215 is sampled using fewer echoes than the latter part when signal has recovered sufficiently. For instance, as illustrated in the adaptive multi-echo sampling scheme 230 shown in FIG. 2C, a two-echo readout can be used for high temporal resolution sampling of the initial part of the magnetization recovery curve 220 for efficient T1 estimation followed by a 3 or more echo readout for the latter part.

The use of a radial trajectory also allows generating a trace of the breathing signal and binning the acquired data to reconstruct images at different motion states. By designing a binning strategy that allows good temporal sampling of the recovery curve 215, the technique described herein can be made more suitable for free breathing acquisitions.

Figure 3:
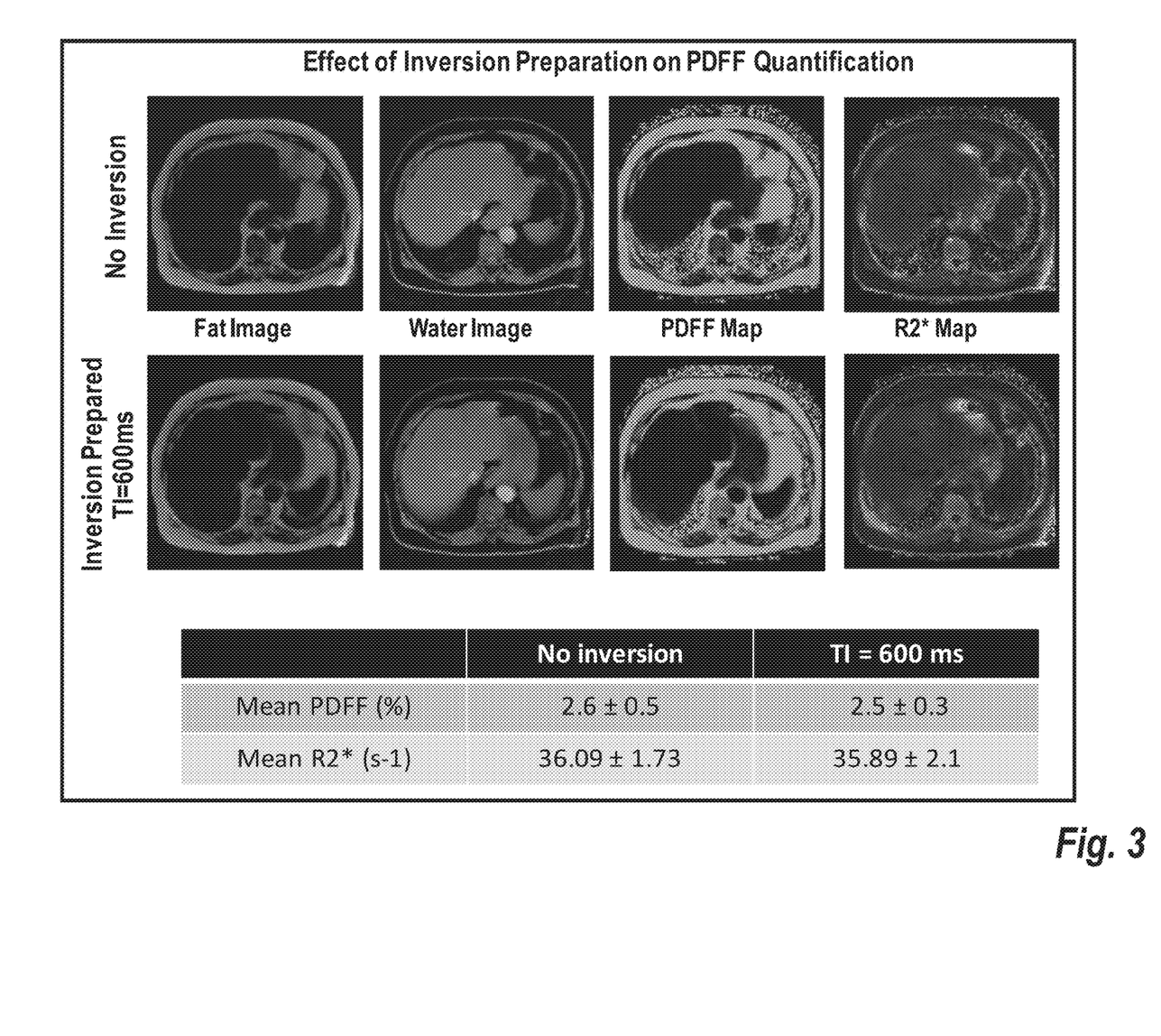
FIG. 3 shows example PDFF and R2* maps from a normal volunteer without any inversion preparation and at inversion time (TI)=600 ms.

The effect of magnetization preparation on PDFF and R2* quantification is demonstrated in FIG. 3. This example shows PDFF and R2* maps from a normal volunteer acquired using a multi-echo radial FLASH pulse sequence without inversion preparation and at an inversion time of 600 ms. The estimated PDFF and R2* values from regions of interest (ROIs) in the liver indicate no effect of inversion preparation on fat water quantification accuracy.

The signal at each voxel in an inversion recovery Look-Locker acquisition can be expressed as follows:

$$S(TE, TI) = [S_w(TE, TI) + S_F(TE, TI)]e^{2\pi i \phi TE} = \quad [1]$$

$$\left[ Mxy_w(TI, T1_w)e^{-\frac{TE}{T2_w^*}} + \left( Mxy_f(TI, T1_f)e^{-\frac{TE}{T2_f^*}} * Ce^{2\pi i \Delta f TE} \right) \right] e^{2\pi i \phi(TE)}$$

where $Mxy_w$ and $Mxy_f$ are the observed transverse magnetization for the water and fat components and $T2_w^*$, $T2_f^*$, $T1_w$, $T1_f$ are the T2* and T1 relaxation times for the two components. C and $\Delta f$ are the relative amplitude and frequency offset of the fat signal respectively and $\phi(TE)$ corresponds to the phase offset of the acquisition at echo time TE. For acquisitions with more than two echoes it is reasonable to assume a linear dependence of $\phi(TE)$ in TE, where the intercept is relevant in case $M_{xy}$ is considered real-valued and the slope corresponds to the off-center frequency.

With Look-Locker sampling, the transverse magnetization for each component can be modeled as:

$$Mxy_\#(TI, T1_\#, M_{0\#}) = M_{0\#} f(TI, T1_\#, B1_{eff}, \alpha) \quad [2]$$

where $f(.)$ is a function such as the SNAPSHOT-FLASH model or Bloch equation model representing the signal evolution over different inversion times. Both of these models are generally known in the art, and thus not described in further detail herein.

Figure 4A:
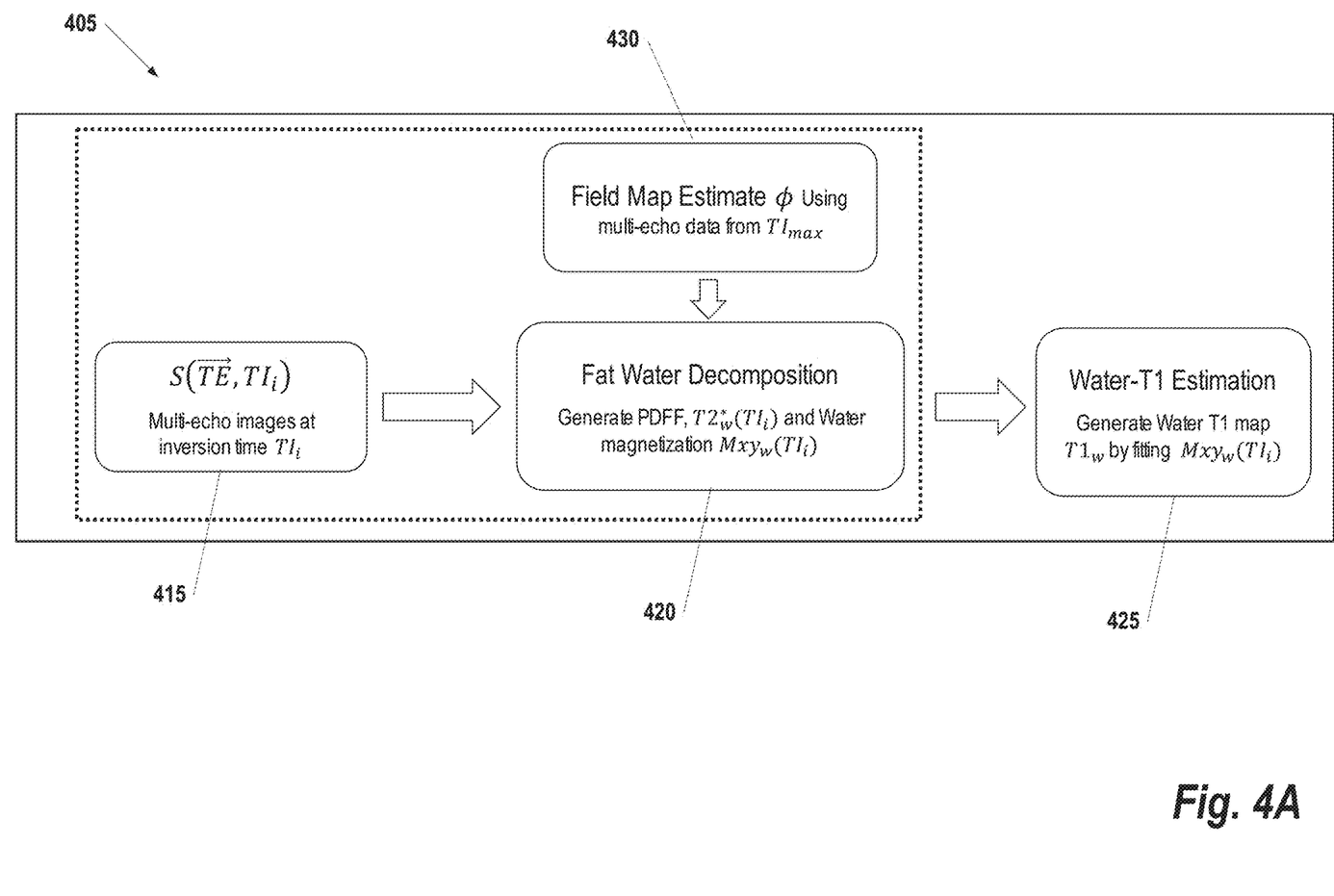
FIG. 4A shows a sequential fitting approach for Water-T1 estimation, according to some embodiments.
Figure 4B:
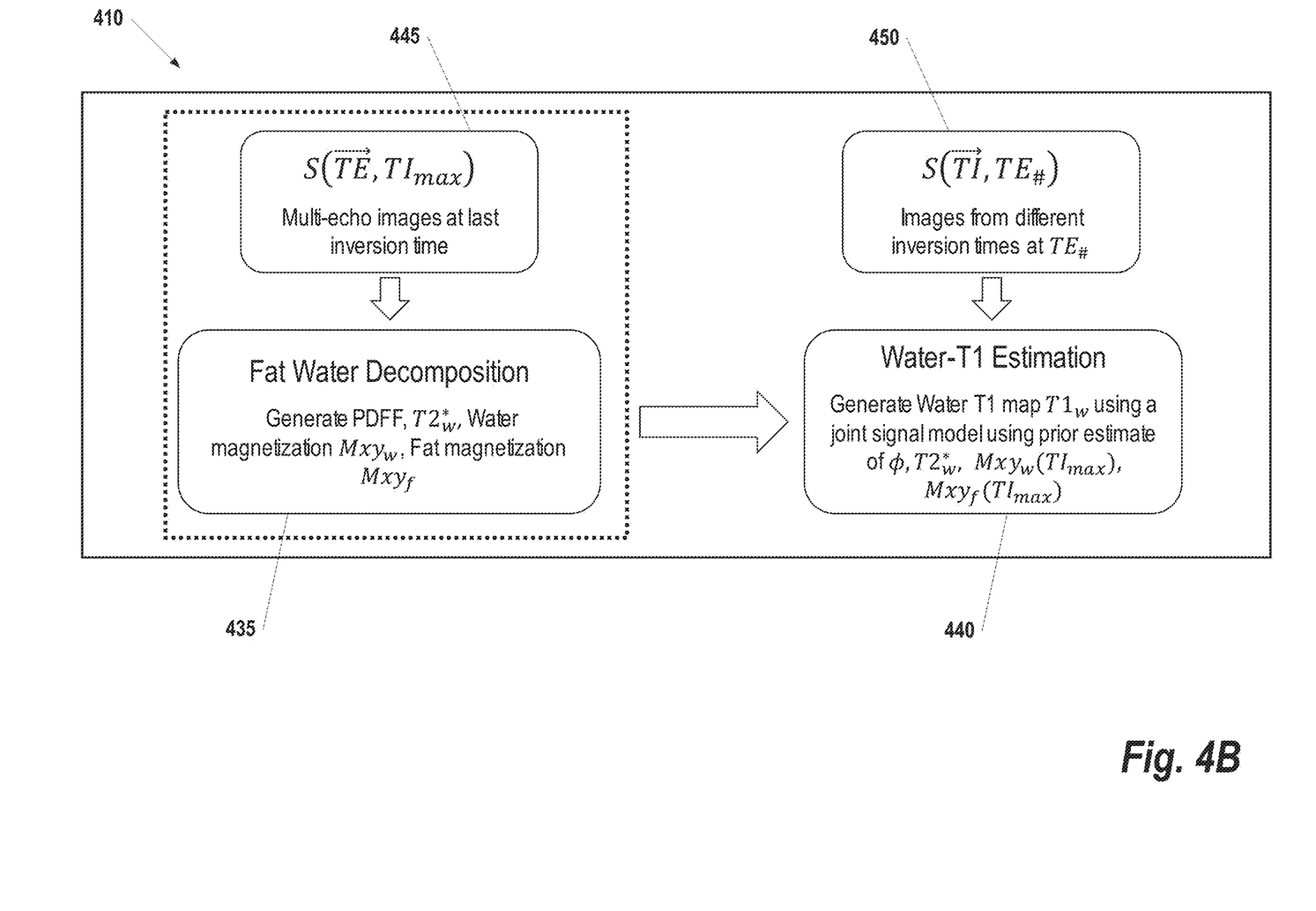
FIG. 4B shows a joint fitting scheme for Water-T1 estimation, according to some embodiments.

FIGS. 4A and 4B show two alternative techniques for Water-T1 Estimation that may be applied in different embodiments of the present invention. FIG. 4A illustrates a sequential fitting approach 405 where multi-echo fat water separation algorithms are used to estimate PDFF and T2* at each TI, followed by fitting the water-only signal to generate the T1, map 425. Various multi-echo fat water separation algorithms known in the art may be utilized. Example multi-echo fat water separation algorithms are described in U.S. Pat. No. 9,823,322 entitled "Method and apparatus for magnetic resonance data acquisition using a multipoint dixon technique," issued Nov. 21, 2017, the entirety of which is incorporated herein by reference.

Continuing with reference to FIG. 4A, the background field map is estimated 430 once using multi-echo data 415 from the last TI time ($TI_{max}$) and used for other inversion times. It is also conceivable that the data are binned differently in an initial reconstruction, e.g., using more spokes for the last timepoint. This increases the signal-to-noise ratio (SNR) and decreases under-sampling artifacts for the estimation of the parameter maps that are assumed to be constant for all inversion times, such as $B1_{eff}$ and $\phi(TE)$.

FIG. 4B illustrates a multi-parameter joint fitting scheme 410. Here, Equation [2] is re-formulated as:

$$Mxy_\#(TI,T1_\#,M_{0\#}) = M_0 Mxy_\#(TI_{max}) f(TI,T1_\#,B1_{eff},\alpha) \quad [3]$$

where $Mxy_\#(TI_{max})$ is the magnetization of individual components at the last TI sampled. A multi-echo fat water decomposition 435 is first performed using the multi-echo data at $TI_{max}$ 445 to estimate $\phi$, T2* and Mxy for the two components. Using these values, along with Equations [3] and [1] the $T1_w$, $T1_f$ and scaling factor $M_0$ are estimated 440 with images at different inversion times 450, as shown in FIG. 4B. The approach also suggests using a different number of echoes for the last timepoint and the initial curve. Using a two echo scheme in the early part of the curve may be sufficient to determine the T1 and cope with the fast recovery.

Figure 5A:
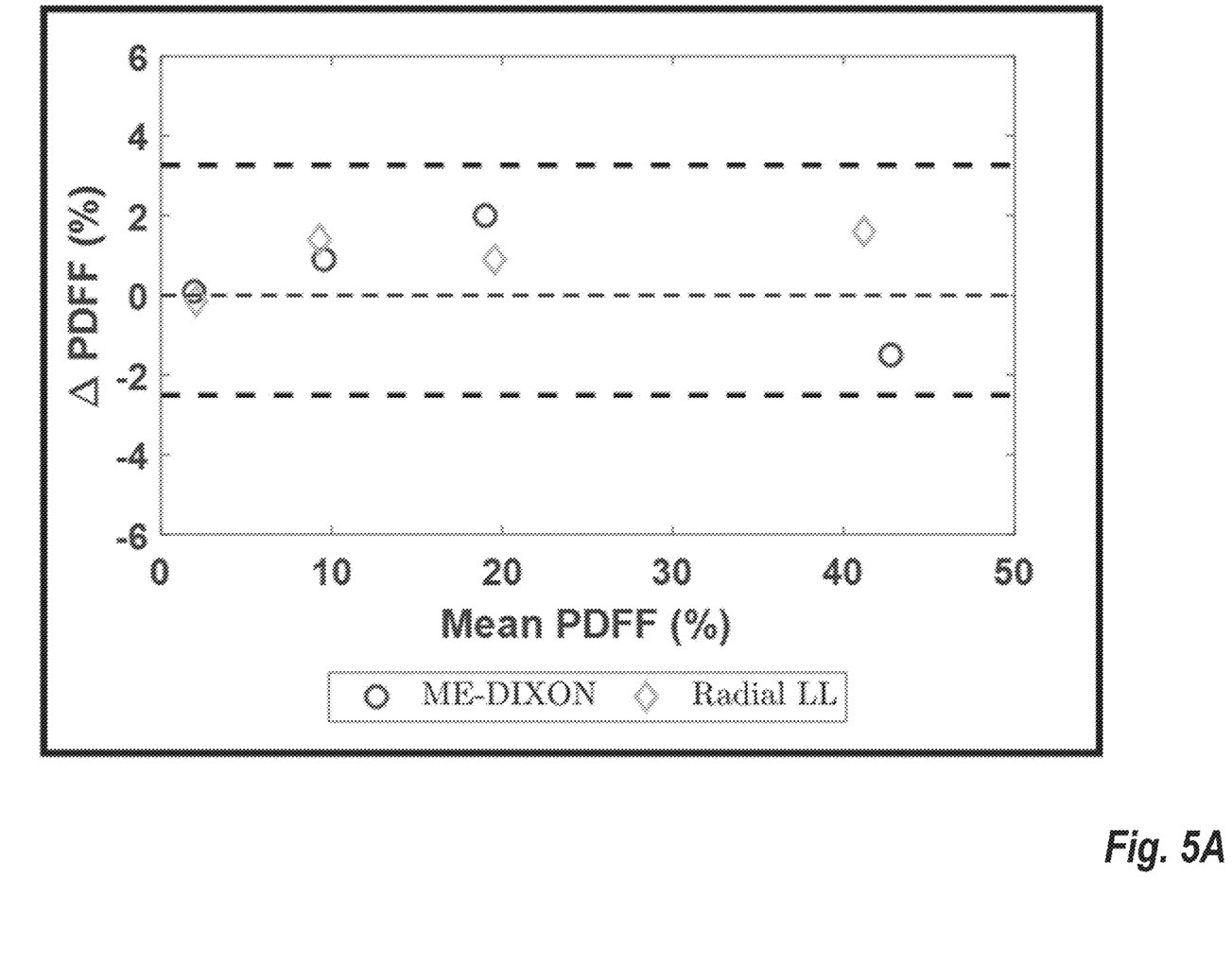
FIG. 5A presents Bland-Altman plots illustrating the mean error in PDFF, according to some embodiments.
Figure 5B:
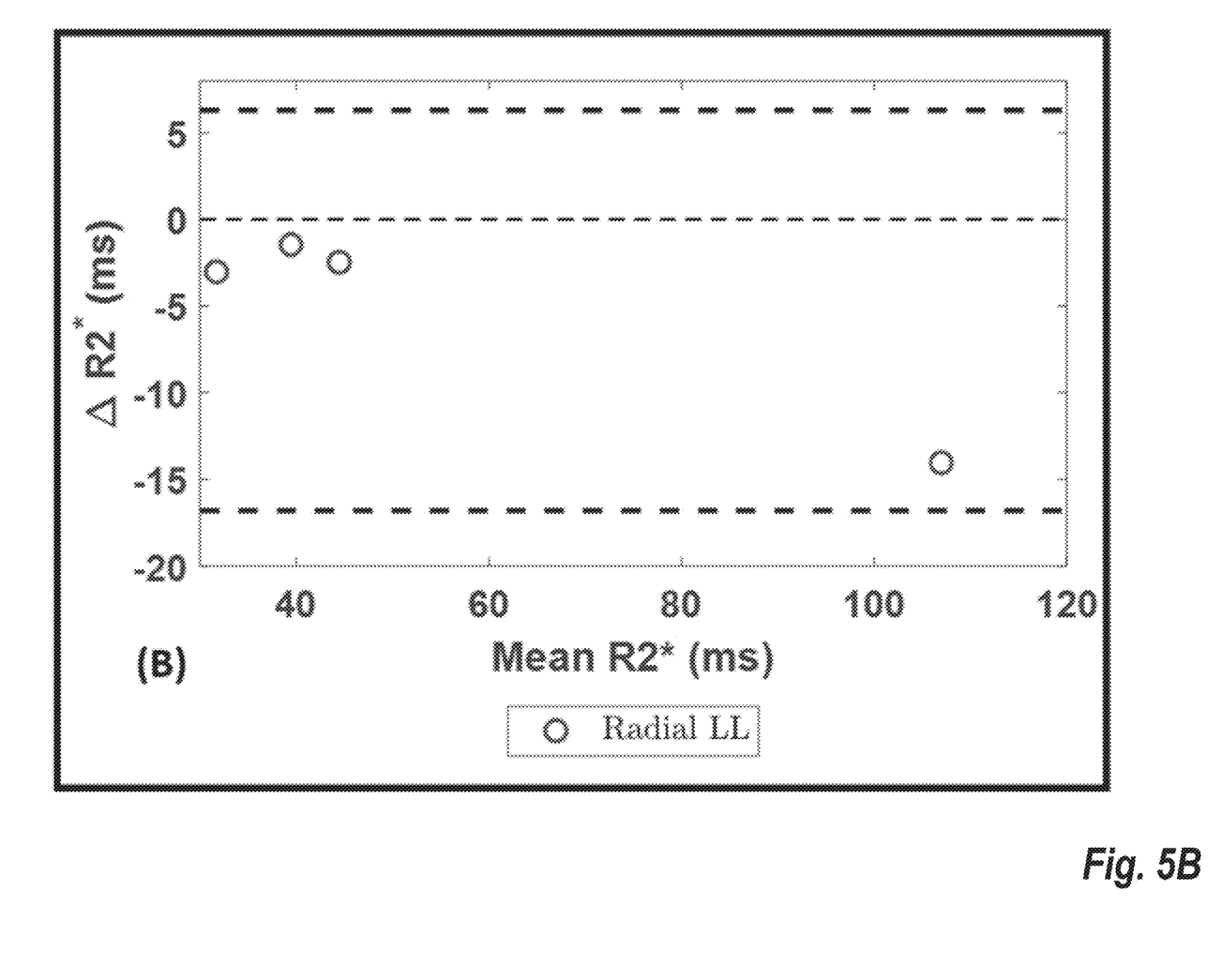
FIG. 5B presents Bland-Altman plots illustrating the mean error in R2* estimates from the multi-echo radial Look-Locker sequence compared to the reference, according to some embodiments.
Figure 5C:
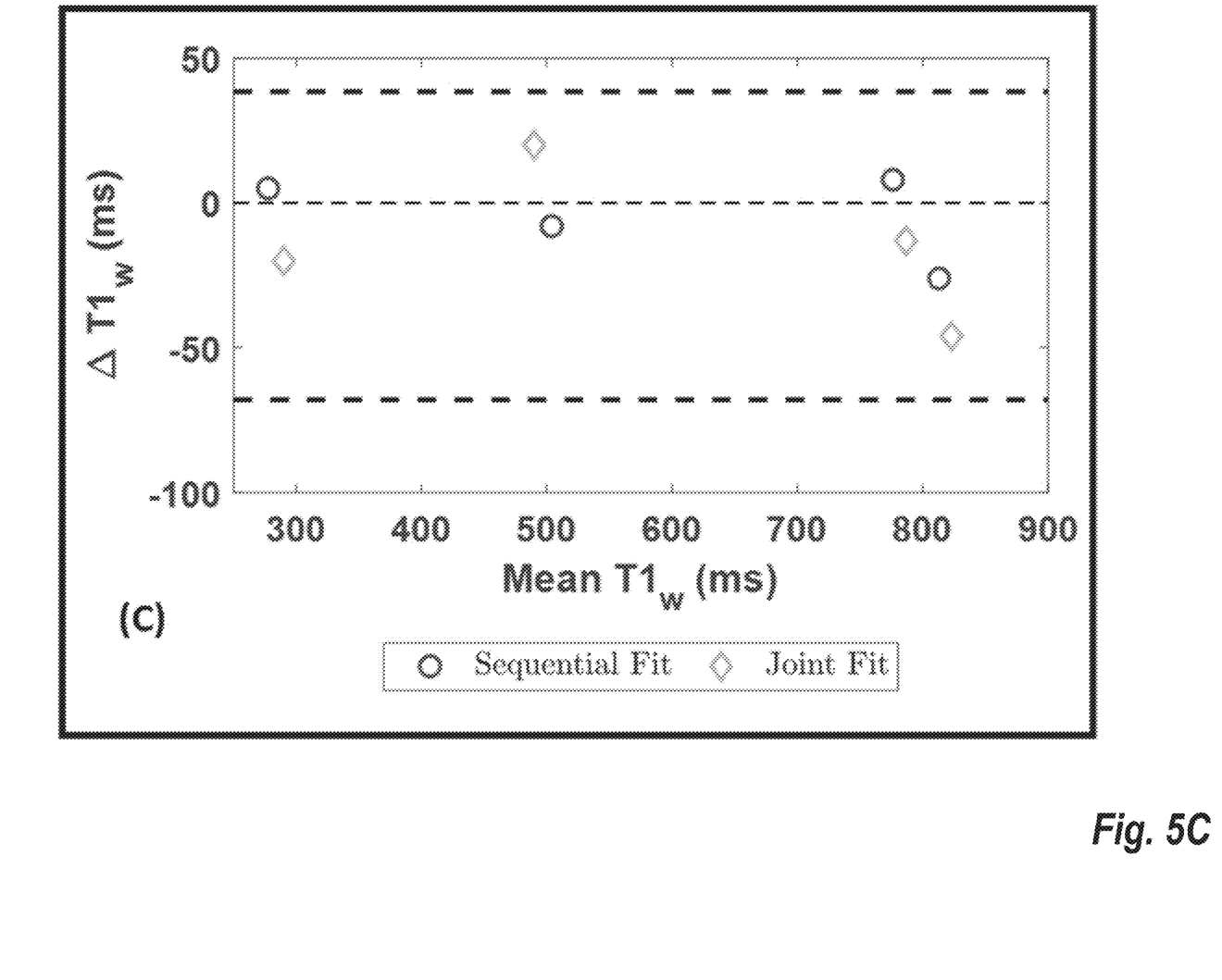
FIG. 5C presents Bland-Altman plots illustrating the mean error in T1w estimates from the two fitting techniques shown in FIGS. 4A and 4B compared to the spin echo reference, according to some embodiments.

FIGS. 5A and 5B are Bland-Altman plots that show PDFF and R2* values obtained using the prototype multi-echo radial Look-Locker sequence compared to the reference Cartesian multi-echo DIXON acquisition. Note that the PDFF estimates are comparable to the ME-DIXON. FIG. 5C shows T1, estimates from the two fitting techniques discussed above with reference to FIGS. 4A and 4B, compared to the fat suppressed multi-TR spin echo reference. As shown in FIG. 5C, each of the proposed fitting algorithms has than 6% relative T1w estimation error.

Figure 6:
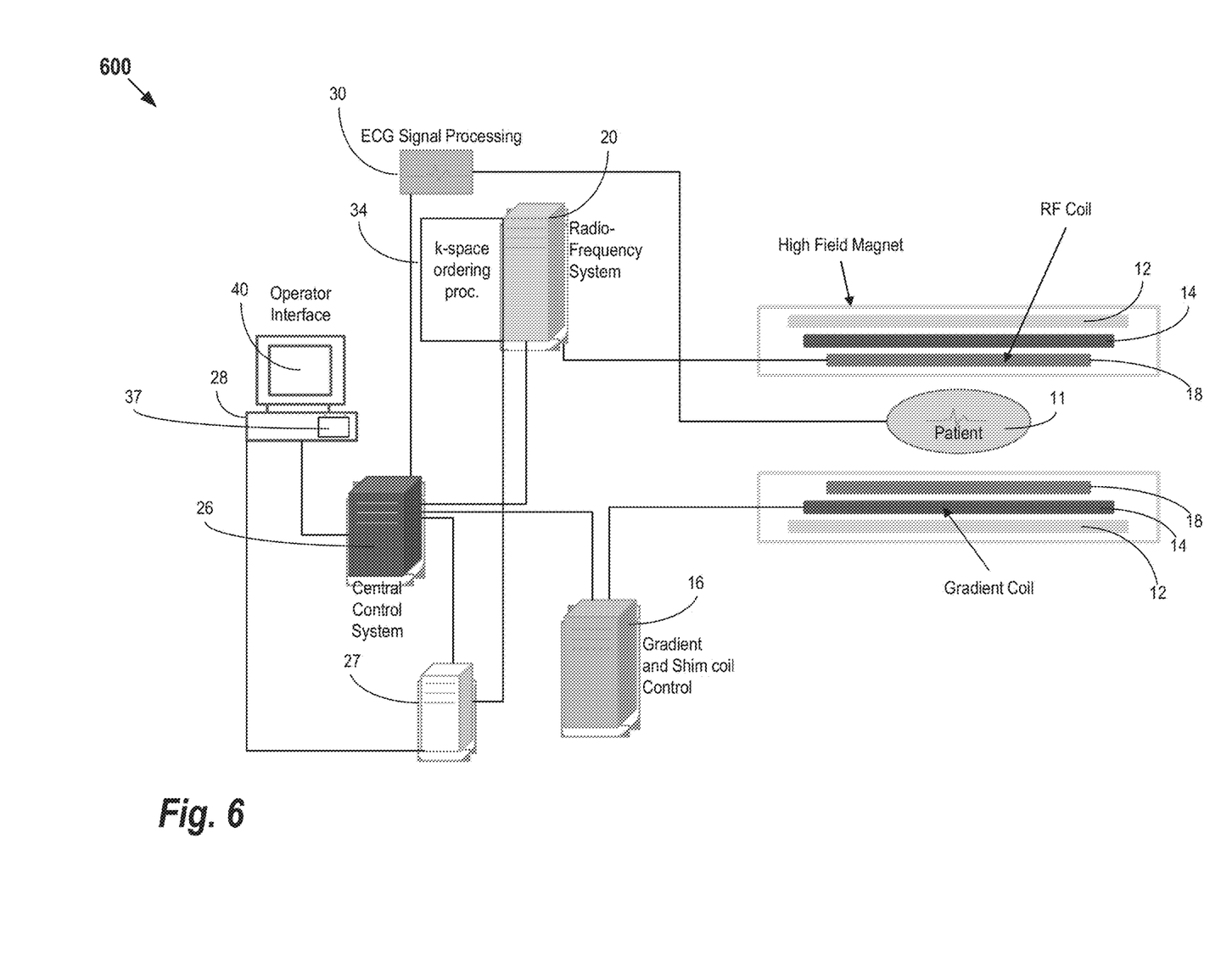
FIG. 6 shows a system for ordering acquisition of frequency domain components representing magnetic resonance (MR) image data for storage in a k-space storage array, as used by some embodiments of the present invention.

FIG. 6 shows a system 600 for ordering acquisition of frequency domain components representing MR image data for storage in a k-space storage array, as used by some embodiments of the present invention. In system 600, magnetic coils 12 create a static base magnetic field in the body of patient 11 to be imaged and positioned on a table. Within the magnet system are gradient coils 14 for producing position dependent magnetic field gradients superimposed on the static magnetic field. Gradient coils 14, in response to gradient signals supplied thereto by a gradient and shim coil control module 16, produce position dependent and shimmed magnetic field gradients in three orthogonal directions and generates magnetic field pulse sequences. The shimmed gradients compensate for inhomogeneity and variability in an MR imaging device magnetic field resulting from patient anatomical variation and other sources. The magnetic field gradients include a slice-selection gradient magnetic field, a phase-encoding gradient magnetic field and a readout gradient magnetic field that are applied to patient 11.

Further RF (radio frequency) module 20 provides RF pulse signals to RF coil 18, which in response produces magnetic field pulses which rotate the spins of the protons in the imaged body of the patient 11 by ninety degrees or by one hundred and eighty degrees for so-called "spin echo" imaging, or by angles less than or equal to 90 degrees for so-called "gradient echo" imaging. Gradient and shim coil control module 16 in conjunction with RF module 20, as directed by central control unit 26, control slice-selection, phase-encoding, readout gradient magnetic fields, radio frequency transmission, and magnetic resonance signal detection, to acquire magnetic resonance signals representing planar slices of patient 11. For example, as described in greater detail below, in some embodiments, the central control unit 26 directs the various components of the system 600 to acquire radial k-space data using free-breathing stack-of-radial MRI pulse sequence described above with reference to FIGS. 1A-1C.

In response to applied RF pulse signals, the RF coil 18 receives MR signals, i.e., signals from the excited protons within the body as they return to an equilibrium position established by the static and gradient magnetic fields. The MR signals are detected and processed by a detector within RF module 20 and k-space component processor unit 34 to provide an MR dataset to an image data processor for processing into an image. In some embodiments, the image data processor is located in central control unit 26. However, in other embodiments such as the one depicted in FIG. 6, the image data processor is located in a separate unit 27. ECG synchronization signal generator 30 provides ECG signals used for pulse sequence and imaging synchronization. A two or three dimensional k-space storage array of individual data elements in k-space component processor unit 34 stores corresponding individual frequency components comprising an MR dataset. The k-space array of individual data elements has a designated center and individual data elements individually have a radius to the designated center.

A magnetic field generator (comprising coils 12, 14 and 18) generates a magnetic field for use in acquiring multiple individual frequency components corresponding to individual data elements in the storage array. The individual frequency components are successively acquired in an order in which radius of respective corresponding individual data elements increases and decreases along a substantially spiral path as the multiple individual frequency components is sequentially acquired during acquisition of an MR dataset representing an MR image. A storage processor in the k-space component processor unit 34 stores individual frequency components acquired using the magnetic field in corresponding individual data elements in the array. The radius of respective corresponding individual data elements alternately increases and decreases as multiple sequential individual frequency components are acquired. The magnetic field acquires individual frequency components in an order corresponding to a sequence of substantially adjacent individual data elements in the array and magnetic field gradient change between successively acquired frequency components is substantially minimized.

Central control unit 26 uses information stored in an internal database to process the detected MR signals in a coordinated manner to generate high quality images of a selected slice(s) of the body (e.g., using the image data processor) and adjusts other parameters of system 100. The stored information comprises predetermined pulse sequence and magnetic field gradient and strength data as well as data indicating timing, orientation and spatial volume of gradient magnetic fields to be applied in imaging. Generated images are presented on display of the operator interface 40. Computer 28 of the operator interface includes a graphical user interface (GUI) enabling user interaction with central control unit 26 and enables user modification of magnetic resonance imaging signals in substantially real time. Display processor 37 processes the magnetic resonance signals to provide image representative data for display on operator interface 40, for example.

The embodiments of the present disclosure may be implemented with any combination of hardware and software. In addition, the embodiments of the present disclosure may be included in an article of manufacture (e.g., one or more computer program products) having, for example, computer-readable, non-transitory media. The media has embodied therein, for instance, computer readable program code for providing and facilitating the mechanisms of the embodiments of the present disclosure. The article of manufacture can be included as part of a computer system or sold separately.

The term "computer readable medium" as used herein refers to any medium that participates in providing instructions to the processor for execution. A computer readable medium may take many forms including, but not limited to, non-volatile media, volatile media, and transmission media. Non-limiting examples of non-volatile media include optical disks, solid state drives, magnetic disks, and magneto-optical disks, such as hard disk or removable media drive. One non-limiting example of volatile media is dynamic memory. Non-limiting examples of transmission media include coaxial cables, copper wire, and fiber optics, including the wires that make up one or more buses. Transmission media may also take the form of acoustic or light waves, such as those generated during radio wave and infrared data communications.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

An executable application, as used herein, comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters.

The functions and process steps herein may be performed automatically or wholly or partially in response to user command. An activity (including a step) performed automatically is performed in response to one or more executable instructions or device operation without user direct initiation of the activity.

The system and processes of the figures are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. As described herein, the various systems, subsystems, agents, managers and processes can be implemented using hardware components, software components, and/or combinations thereof. No claim element herein is to be construed under the provisions of 35 U.S.C. 112(f), unless the element is expressly recited using the phrase "means for."

We claim:

1. A method for using a multi-echo magnetic resonance imaging (MRI) that simultaneously quantifies T1 and fat fraction in an anatomical region of interest, the method comprising:

performing a radial single shot multi-echo acquisition of the anatomical region of interest, wherein the radial single shot multi-echo acquisition comprises:
applying a preparation pulse to invert longitudinal magnetization of the anatomical region of interest,
acquiring a plurality of multi-echo radial readouts at different echo times (TE) after the preparation pulse, and
continuously sampling a magnetization recovery curve using the plurality of radial readouts to yield a plurality of radial spokes;
grouping the radial spokes for each TE together to generate under-sampled k-space data for each TE; and
reconstructing the under-sampled k-space data into a plurality of multi-echo images corresponding to the different echo times;
applying one or more curve fitting algorithms to the multi-echo images to generate a water-only T1 map and a proton density fat fraction (PDFF) measurement to fit the magnetization recovery curve.

2. The method of claim 1, wherein the magnetization recovery curve is sampled uniformly for each TE.

3. The method of claim 1, wherein
the magnetization recovery curve is divided into an initial part and a remaining part;
the magnetization recovery curve is sampled using an adaptive non-uniform multi-echo sampling scheme where (a) the initial part of the magnetization recovery curve is sampled using a subset of the plurality of radial readouts and (a) the remaining part of the magnetization recovery curve is sampled using all of the plurality of radial readouts.

4. The method of claim 1, wherein the under-sampled k-space data is reconstructed using one or more iterative reconstruction algorithms.

5. The method of claim 1, wherein the fitting algorithms generate a T2* measurement with the water-only T1 map and the PDFF measurement.

6. The method of claim 5, wherein the fitting algorithms comprise:
using a fat-water separation algorithm to quantify the PDFF measurement, the T2* measurement, and a water magnetization measurement at each inversion time (TI);
generating the water-only T1 map by fitting the water magnetization measurement.

7. The method of claim 6, wherein the fat-water separation algorithm is parameterized by a background field map is estimated once using the under-sampled k-space data corresponding to a last TI time ($TI_{max}$).

8. The method of claim 5, wherein the fitting algorithms comprise:
identifying a subset of the multi-echo images corresponding to a last TI time ($TI_{max}$)
using a fat-water separation algorithm to quantify the PDFF measurement, the T2* measurement, and a water magnetization measurement at $TI_{max}$ based on the subset of the multi-echo images;
generating the water-only T1 map by fitting the water magnetization measurement using the PDFF measurement and the T2* measurement as priors.

9. The method of claim 1, wherein the preparation pulse is an inversion recovery pulse.

10. The method of claim 1, wherein the preparation pulse is a saturation pulse.

11. A multi-echo magnetic resonance imaging (MRI) system for simultaneously quantifying T1 and fat fraction in an anatomical region of interest, the system comprising:
- an imaging device configured to perform a radial single shot multi-echo acquisition of the anatomical region of interest, wherein the radial single shot multi-echo acquisition comprises:
  - applying a preparation pulse to invert longitudinal magnetization of the anatomical region of interest,
  - acquiring a plurality of multi-echo radial readouts at different echo times (TE) after the preparation pulse, and
  - continuously sampling a magnetization recovery curve using the plurality of radial readouts to yield a plurality of radial spokes;
- one or more computers configured to:
  - group the radial spokes for each TE together to generate under-sampled k-space data for each TE; and
  - reconstruct the under-sampled k-space data into a plurality of multi-echo images corresponding to the different echo times;
  - apply one or more curve fitting algorithms to the multi-echo images to generate a water-only T1 map and a proton density fat fraction (PDFF) measurement to fit the magnetization recovery curve.

12. The system of claim 11, wherein the magnetization recovery curve is sampled uniformly for each TE.

13. The system of claim 11, wherein
the magnetization recovery curve is divided into an initial part and a remaining part;
the magnetization recovery curve is sampled using an adaptive non-uniform multi-echo sampling scheme where (a) the initial part of the magnetization recovery curve is sampled using a subset of the plurality of radial readouts and (a) the remaining part of the magnetization recovery curve is sampled using all of the plurality of radial readouts.

14. The system of claim 11, wherein the under-sampled k-space data is reconstructed using one or more iterative reconstruction algorithms.

15. The system of claim 11, wherein the fitting algorithms generate a T2* measurement with the water-only T1 map and the PDFF measurement.

16. The system of claim 15, wherein the fitting algorithms comprise:
- using a fat-water separation algorithm to quantify the PDFF measurement, the T2* measurement, and a water magnetization measurement at each inversion time (TI);
- generating the water-only T1 map by fitting the water magnetization measurement.

17. The system of claim 16, wherein the fat-water separation algorithm is parameterized by a background field map is estimated once using the under-sampled k-space data corresponding to a last TI time ($TI_{max}$).

18. The system of claim 15, wherein the fitting algorithms comprise:
- identifying a subset of the multi-echo images corresponding to a last TI time ($TI_{max}$)
- using a fat-water separation algorithm to quantify the PDFF measurement, the T2* measurement, and a water magnetization measurement at $TI_{max}$ based on the subset of the multi-echo images;
- generating the water-only T1 map by fitting the water magnetization measurement using the PDFF measurement and the T2* measurement as priors.

* * * * *